US008283462B2

(12) United States Patent
Zhou et al.

(10) Patent No.: US 8,283,462 B2
(45) Date of Patent: Oct. 9, 2012

(54) GROUP OF NUCLEIC ACID FRAGMENTS FOR PREVENTION OF HIV INFECTION OR AIDS AND THE USAGE THEREOF

(75) Inventors: Zhiwen Zhou, Beijing (CN); Yuxia Feng, Beijing (CN); Conglin Zuo, Beijing (CN); Yuejuan Li, Beijing (CN)

(73) Assignee: Beijing Solobio Genetechnology Company Ltd., Beijing (CN)

( * ) Notice: Subject to any disclaimer, the term of this patent is extended or adjusted under 35 U.S.C. 154(b) by 0 days.

(21) Appl. No.: 12/987,597

(22) Filed: Jan. 10, 2011

(65) Prior Publication Data

US 2011/0217361 A1     Sep. 8, 2011

Related U.S. Application Data

(62) Division of application No. 10/539,446, filed as application No. PCT/CN03/01068 on Dec. 16, 2003, now Pat. No. 7,906,641.

(30) Foreign Application Priority Data

Dec. 18, 2002   (CN) .................................. 02 1 56785

(51) Int. Cl.
    C07H 21/02      (2006.01)
    C07H 21/04      (2006.01)
    C12Q 1/68       (2006.01)
    C12P 19/34      (2006.01)
    C12N 15/58      (2006.01)

(52) U.S. Cl. ....... 536/24.5; 435/6; 435/91.1; 435/91.31; 435/458; 536/23.1; 536/24.32

(58) Field of Classification Search ............. 435/6, 91.1, 435/91.31, 458; 514/44; 536/23.1, 24.5, 536/24.32

See application file for complete search history.

(56) References Cited

U.S. PATENT DOCUMENTS

| 5,958,768 | A | 9/1999 | Kraus et al. |
| 5,965,726 | A | 10/1999 | Pavlakis et al. |
| 6,503,705 | B1 | 1/2003 | Kozal et al. |
| 6,506,559 | B1 | 1/2003 | Fire et al. |
| 7,129,041 | B2 | 10/2006 | Merigan et al. |
| 2002/0031521 | A1 | 3/2002 | Spetz-Holmgren et al. |
| 2003/0157693 | A1* | 8/2003 | Verdin et al. ............... 435/235.1 |
| 2003/0175950 | A1 | 9/2003 | McSwiggen |
| 2003/0203868 | A1* | 10/2003 | Bushman et al. ............... 514/44 |

FOREIGN PATENT DOCUMENTS

| EP | 0403333 A2 | 12/1990 |
| JP | 2006-502694 A | 1/2006 |
| WO | WO 98/59074 * | 6/1998 |
| WO | 02/44321 A2 | 6/2002 |
| WO | 03/070193 A2 | 8/2003 |

OTHER PUBLICATIONS

Sudhir Agrawal et al., "Antisense therapeutics: is it as simple as complementary base recognition?", Molecular Medicine Today, 2000, 6: 72-81.
Andrea D. Branch, "A good antisense molecule is hard to find", TIBS, 1998, 23: 45-50.
John Capodici et al., "Inhibition of HIV-1 Infection by Small Interfering RNA-Mediated RNA Interference", The Journal of Immunology, 2002, 169: 5196-5201.
Traian V. Chirila et al., "The use of synthetic polymers for delivery of therapeutic antisense oligodeoxynucleotides", Biomaterials, 2002, 23: 321-342.
Glen A. Coburn et al., "Potent and Specific Inhibition of Human Immunodeficiency Virus Type 1 Replication by RNA Interference", The Journal of Virology, 2002, 76(18): 9225-9231.
Stanley T. Crooke et al., "Progress in Antisense Technology", Annu. Rev. Med., 2004, 55:61-95.
European Office Action dated Feb. 19, 2008, in European Patent Application No. 03782054.5.
Jean-Marc Jacque et al., "Modulation of HIV-1 replication by RNA interference", Nature, 2002, 418: 435-438.
Japanese Office Action dated Feb. 17, 2009, in Japanese Patent Application No. 2004-559574.
Nan Sook Lee et al., "Expression of small interfering RNAs targeted against HIV-1 rev transcripts in human cells", Nature Biotechnology, 2002, 20: 500-505.
Carl D. Novina et al., "siRNA-directed inhibition of HIV-1 infection", Nature Medicine, 2002, 8(7): 681-686.
Office Action issued in corresponding European Patent Application No. 03782054.5 on Apr. 22, 2010 (in the name of Beijing Joinn Pharmaceutical Center).
Joanna B. Opalinska et al., "Nucleic-Acid Therapeutics: Basic Principles and Recent Applications", Nature Reviews, 2002, 1: 503-514.
Wee-Sung Park et al., "Prevention of HIV-1 infection in human peripheral blood mononuclear cells by specific RNA interference", Nucleic Acids Research, 2002, 30(22): 4830-4835.
Alessio Peracchi, "Prospects for antiviral ribozymes and deoxyribozymes", Rev. Med. Virol., 2004, 14: 47-64.
Dianne S. Schwarz et al., "Asymmetry in the Assembly of the RNAi Enzyme Complex", Cell, 2003, 115: 199-208.
Takuya Yamamoto et al., "Double-Stranded *nef* RNA Interferes with Human Immunodeficiency Virus Type 1 Replication", Microbiol. Immunol., 2002, 46(11): 809-817.
Extended European Search Report issued in corresponding EP Application No. 10158895.2 on Sep. 22, 2010 (in the name of Beijing Solobio Genetechnology Company Ltd.).
European Office Action issued in corresponding EP Application No. 10158895.2 on Jul. 14, 2011 (in the name of Beijing Solobio Genetechnology Company Ltd.).

(Continued)

*Primary Examiner* — Jane Zara
(74) *Attorney, Agent, or Firm* — Sughrue Mion, PLLC

(57) ABSTRACT

The invention provides a group of nucleic acid fragments, shown in the sequence listing, for prevention of HIV infection or AIDS and the usage thereof. In the invention, a series of RNA fragments, which are highly homogenous to all the published HIV gene sequences, were obtained by homology compare. The double-stranded RNA (dsRNA) derived from these fragments can effectively inhibit the expression of the HIV genes. The RNA transcribed by plasmid, also can suppress the expression of the HIV in the cell. After the adenovirus or associated virus which carry DNA corresponding above RNA infect the cell, the transcription dsRNA can inhibit the expression of the HIV genes.

8 Claims, 6 Drawing Sheets

OTHER PUBLICATIONS

Figure 1:
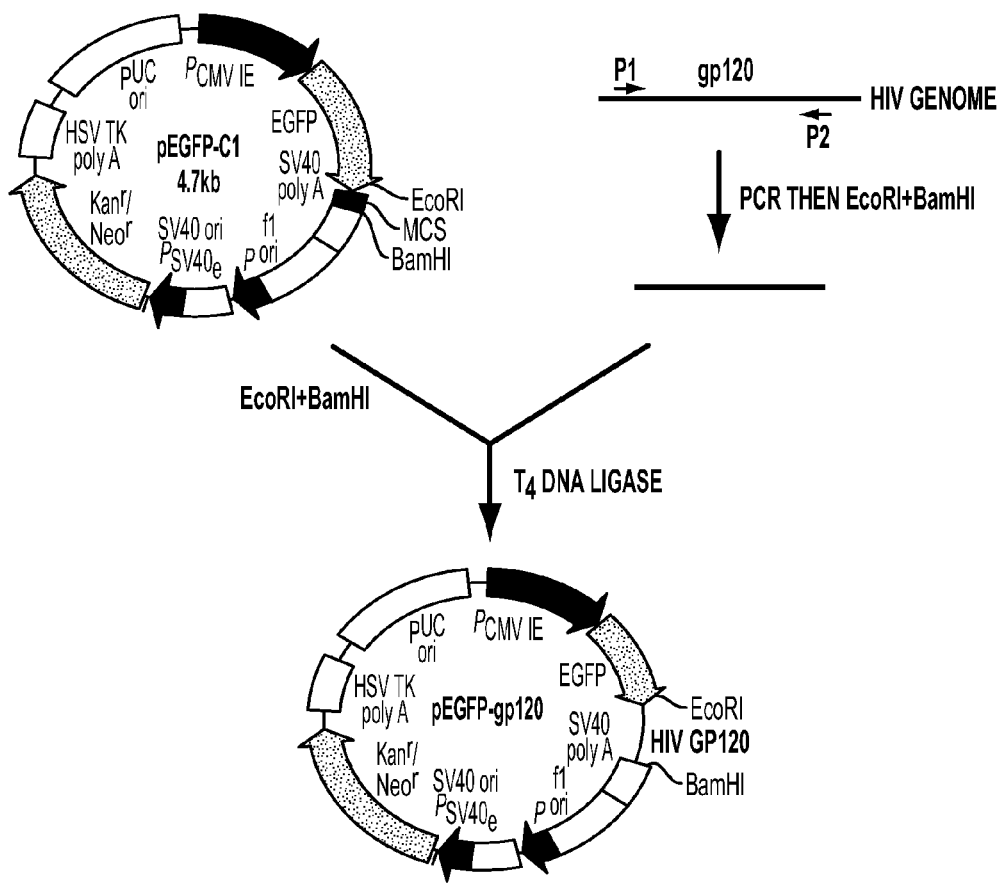

Extended European Search Report issued in corresponding EP Application No. 10158896.0 on Sep. 28, 2010 (in the name of Beijing Solobio Genetechnology Company Ltd.).

European Office Action issued in corresponding EP Application No. 10158896.0 on Jul. 14, 2011 (in the name of Beijing Solobio Genetechnology Company Ltd.).

Extended European Search Report issued in corresponding EP Application No. 10158897.8 on Oct. 4, 2010 (in the name of Beijing Solobio Genetechnology Company Ltd.).

European Office Action issued in corresponding EP Application No. 10158897.8 on Jul. 14, 2011 (in the name of Beijing Solobio Genetechnology Company Ltd.).

Extended European Search Report issued in corresponding EP Application No. 10158898.6 on Oct. 15, 2010 (in the name of Beijing Solobio Genetechnology Company Ltd.).

European Office Action issued in corresponding EP Application No. 10158898.6 on Jul. 14, 2011 (in the name of Beijing Solobio Genetchnology Company Ltd.).

Sayda M. Elbashir et al., "Functional anatomy of siRNAs mediating efficient RNAi in Drosophila melanogaster embryo lysate", The EMBO Journal, 2001, 20(23): 6877-6888.

"HIV-1-JC 5'-LTR-containing fragment PCR primer 527", retrieved from EBI Accession No. AAX03990 on Aug. 25, 2011, 1 page.

Miguel Angel Martinez et al., "RNA interference of HIV replication", Trends in Immunology, 2002, 23(12): 559-561.

M.R. Mautino et al., "Inhibition of HIV-1 replication by novel lentiviral vectors expressing transdominant Rev and HIV-1 env antisense", Gene Therapy, 2002, 9: 421-431.

Paul S. Miller et al., "Studies on anti-human immunodeficiency virus oligonucleotides that have alternating methylphosphonate/phosphodiester linkages", Pharmacology & Therapeutics, 2000, 85: 159-163.

Karin Renneisen et al., "Inhibition of Expression of Human Immunodeficiency Virus-1 in Vitro by Antibody-targeted Liposomes Containing Antisense RNA to the env Region", The Journal of Biological Chemistry, 1990, 265(27): 16337-16342.

Sequence 77 from U.S. Patent No. 5,965,726, retrieved from EBI Accession No. AR079753, accessed online at http://ibis.internal.epo.org/IBIS/exam/dbfetch.jsp?id=EM_PAT:AR079753 on Jun. 9, 2010.

Sequence 95 from U.S. Patent No. 5,965,726 retrieved from EBI Accession No. AR079771, accessed online at http://ibis.internal.epo.org/IBIS/exam/dbfetch.jsp?id=EM_PAT:AR079771 on Jun. 9, 2010.

Sequence 1 from WO 01/79542 retrieved from EBI Accession No. AX283309, accessed online at http://ibis.internal.epo.org/IBIS/exam/dbfetch.jsp?id=EM_PAT:AX283309 on Aug. 25, 2010.

Sequence 5 from WO 00/75181 retrieved from EBI Accession No. AX057060, accessed online on Aug. 25, 2010.

Sequence 7 from WO 00/75181 retrieved from EBI Accession No. AX057062, accessed online at http://ibis.internal.epo.org/IBIS/exam/dbfetch.jsp?id=EM_PAT:AX057062 on Sep. 7, 2010.

Rama M. Surabhi et al., "RNA Interference Directed against Viral and Cellular Targets Inhibits Human Immunodeficiency Virus Type 1 Replication", Journal of Virology, 2002, 76(24): 12963-12973.

"Synthetic HIV-1/2 diagnosis primer", retrieved from EBI Accession No. A31975 on Jun. 9, 2010, 1 page.

* cited by examiner

Contrast                +DsRNA

GROUP OF NUCLEIC ACID FRAGMENTS FOR PREVENTION OF HIV INFECTION OR AIDS AND THE USAGE THEREOF

CROSS-REFERENCE TO RELATED APPLICATIONS

This is a divisional of U.S. patent application Ser. No. 10/539,446, filed Jun. 20, 2005 (allowed), which is a 371 National Stage Entry of PCT/CN03/01068 filed Dec. 16, 2003. The entire disclosures of the prior applications are considered part of the disclosure of the present application and are incorporated herein by reference.

TECHNICAL FIELD

The invention is regarded to a set of oligo-nucleotides against HIV infection and its application in the prevention and treatment of Acquired Immune Deficiency Syndrome (AIDS).

TECHNOLOGY BACKGROUND

Recent findings proved that short double strand RNA function as to interference RNA in a variety of mammalian cells, and gene expression can be specifically knocked down. Viral gene (including HIV) expression can be knocked down by this pathway. Due to the high frequency of mutation in HIV genome, most of the interfere RNA can knock down the gene expression of specific isolates and can not be used as a universal approach in gene therapy of AIDS.

INVENTION DISCLOSURE

The purpose of the invention is to provide a set of nucleotides for the prevention of HIV infection and treatment of AIDS.

The other purpose is to provide the application of the oligo-nucleotides mentioned above.

For the purposes, following approaches were employed.

A set of RNA sequences shown thereafter, or any fragments from the sequences, which demonstrate anti-HIV infection activity and be employed in prevention and treatment of AIDS. The nucleotides include single strand RNA, any fragment derived from the sequences, or double strand RNA derived by annealing of the sequences with its complements sequences.

```
(1) aucaaugaggaagcugcagaaugg;      (SEQ ID NO: 1)

(2) gggaagugacauagcaggaacuacuag;   (SEQ ID NO: 2)

(3) uaaauaaaauaguaagaauguauagcccu; (SEQ ID NO: 3)

(4) uauggguaccugugugga;            (SEQ ID NO: 4)

(5) gccaauucccauacauuauugugc;      (SEQ ID NO: 5)

(6) uuaaauggcagucuagcagaa;         (SEQ ID NO: 6)

(7) accacacacaaggcuacuucccugau;    (SEQ ID NO: 7)

(8) acagccgccuagcauuucaucac;       (SEQ ID NO: 8)

(9) ggauggugcuucaagcuaguaccaguu.   (SEQ ID NO: 9)
```

In the invention, conserved oligo-nucleotides sequences among all the HIV genome published were obtained by homology alignment. HIV gene expression could be knocked down and HIV genome can be degraded when the RNA was to introduced into mammalian cells. Pharmaceuticals derived from the conserved sequences can significantly decrease the drug resistant problems resulted from genomic mutagenesis.

A set of RNA sequences, which may be modified by other nucleotide at the 5' or 3' terminal. Usually UU were added at the 3' end of the RNA fragment to assure the match between RNA with targeted mRNA.

A set of hairpin RNA sequences for the control of HIV infection and for the prevention and treatment of AIDS, the hairpin sequences were derived by the hybridization of the sequences (SEQ ID No. 1~SEQ ID No. 9) or the relevant segments at 5' terminal with their complement sequences, in which RNA sequences and the complement sequences were linked by a non complement sequence. Hairpin-like RNA retains activity of RNA interference, and is particular employed to express interfere RNA in the cell since it is a RNA molecular.

A set of DNA sequences or their fragments which is against HIV infection and be used in the prevention and treatment of AIDS:

1) The DNA sequences or their fragments, which correspond to the RNA sequences shown above or their fragments (SEQ ID No. 1~SEQ ID No. 9 in table 1); or correspond to the double strand RNA sequence formed by hybridization of RNAs shown above with its complement sequence, or, 2) The DNA sequences or their fragments, which correspond to the RNA sequences described in 1) or to their fragments which were modified at their 5' or 3' by adding nucleotides; or 3) A single strand or double strand DNA sequence, which correspond to the hairpin like RNA sequence as described above.

A set of expression vectors including both DNA vectors and RNA vectors against HIV infection and used for the prevention or treatment of AIDS, in which RNA or DNA sequences described above were contained. Interfere RNA can be expressed when the vectors containing the DNA and RNA sequences mentioned above were introduced into cells under the control of regulatory elements. The vectors include RNA vectors and DNA vectors. RNA vectors include but is not limited to retroviral vector, DNA vectors carrying DNA sequences indicated and control elements include Plasmid and viral vectors such as adenovirus associated virus (AAV).

A set of liposomes against HIV infection and for the prevention and treatment of AIDS, in which RNA, DNA sequences as well as the expression vectors indicated above against HIV infection and for AIDS treatment and prevention were coated. Interfere RNA or vectors expressing interfere RNA was introduced into cell by the liposome indicated above.

The approach to fight against HIV infection and for AIDS prevention and treatment, by which the above indicated RNAs, DNAs, expression vectors or liposomes were introduced into eukaryotic cell lines, animals or human beings. E.g. Approaches employing liposome and viral vectors.

The application of the nucleotides in the prevention of HIV infection and AIDS treatment. Pharmaceuticals for diagnosis, prevention and treatment of HIV infection and AIDS were derived from the above mentioned RNAs, DNAs, Expression vectors, liposomes or approaches.

DESCRIPTIONS OF THE APPENDIX FIGURES

FIG. 1. Construction of report plasmid pEGFP-gp120.

Figure 2:
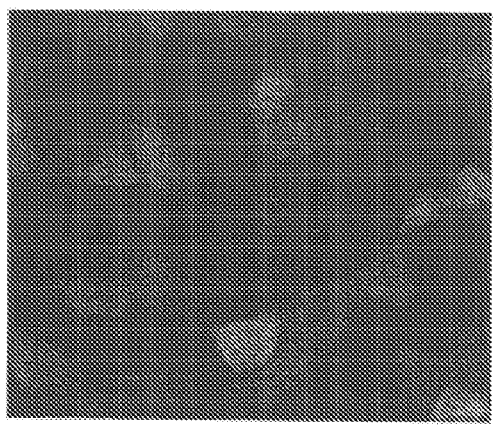
Figure 2:
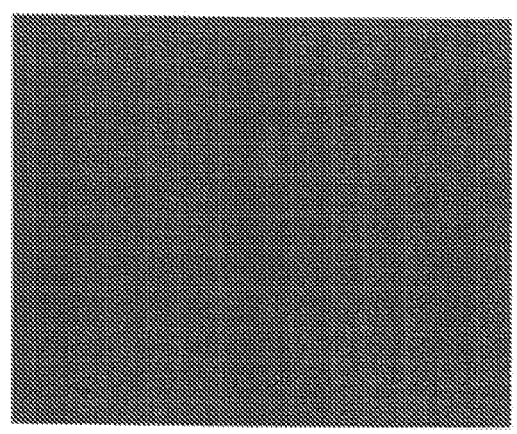

FIG. 2 EGFP-gp120 expression was knocked down by double strand interfere RNA.

Figure 3:
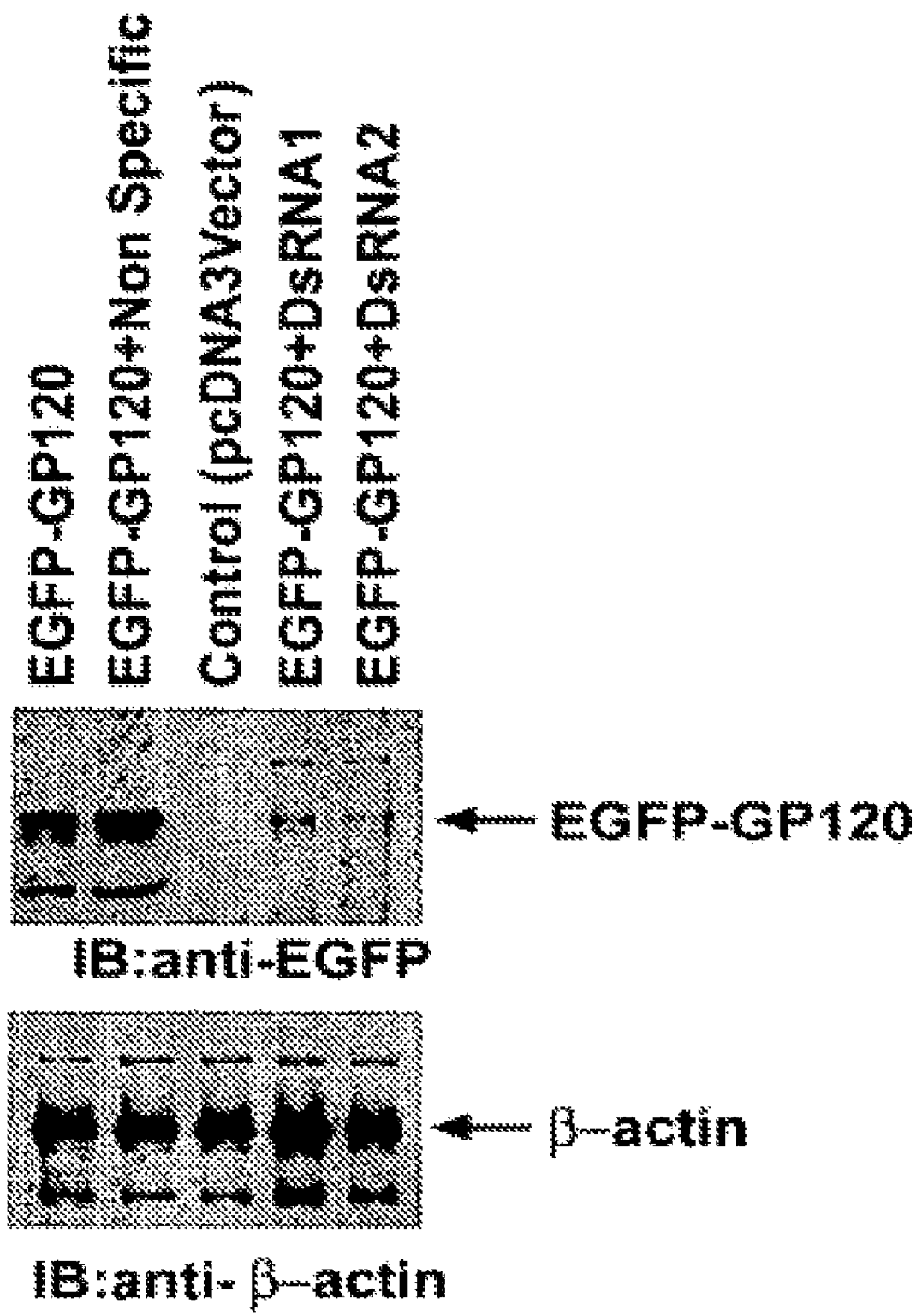

FIG. 3 EGFP-gp120 expression was knocked down by double strand interfere RNA as demonstrated by Western-Blot.

Figure 4:
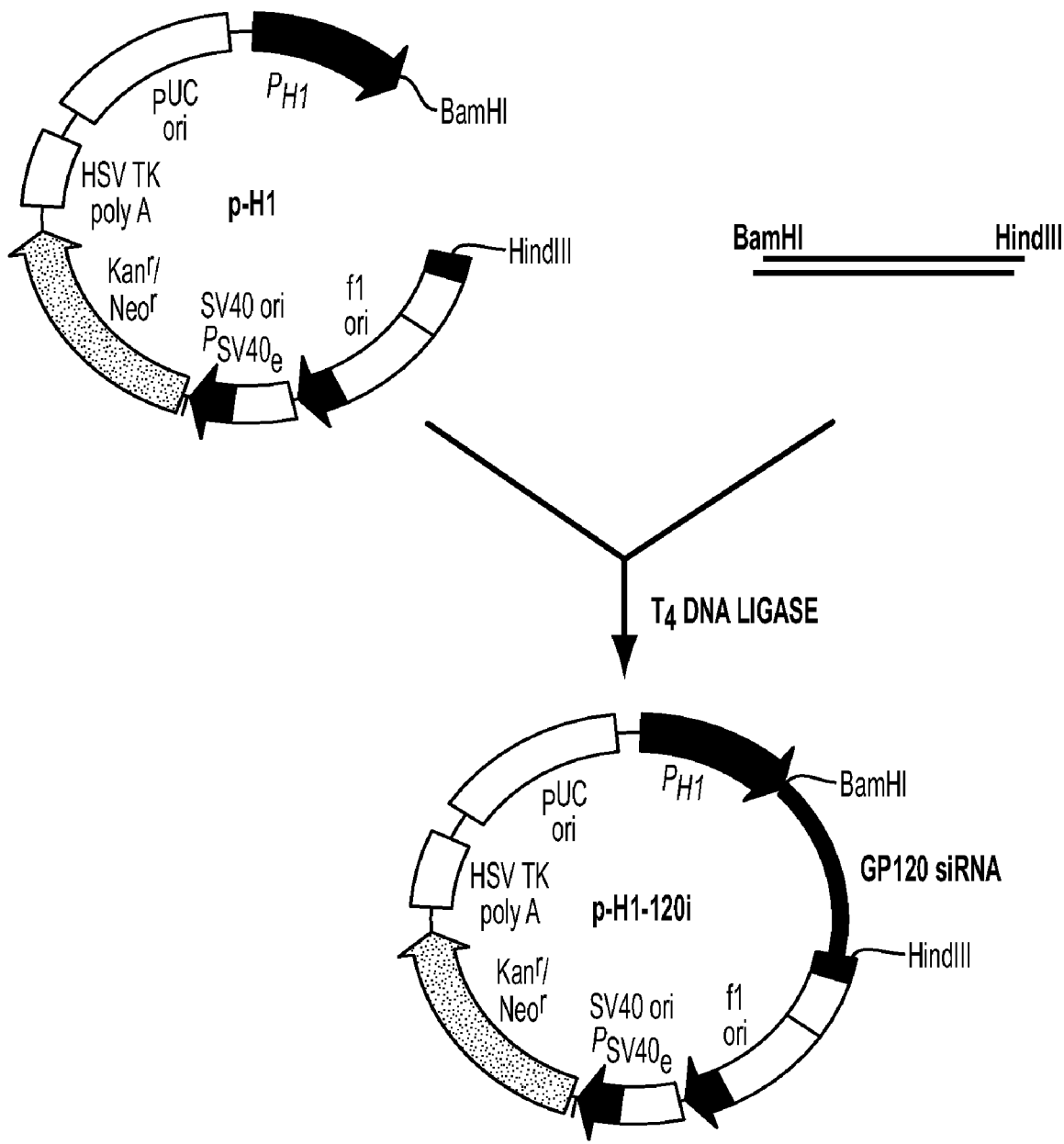

FIG. 4 The construction of p-H1-gp120i from which the hairpin RNA could be expressed in the cells.

Figure 5:
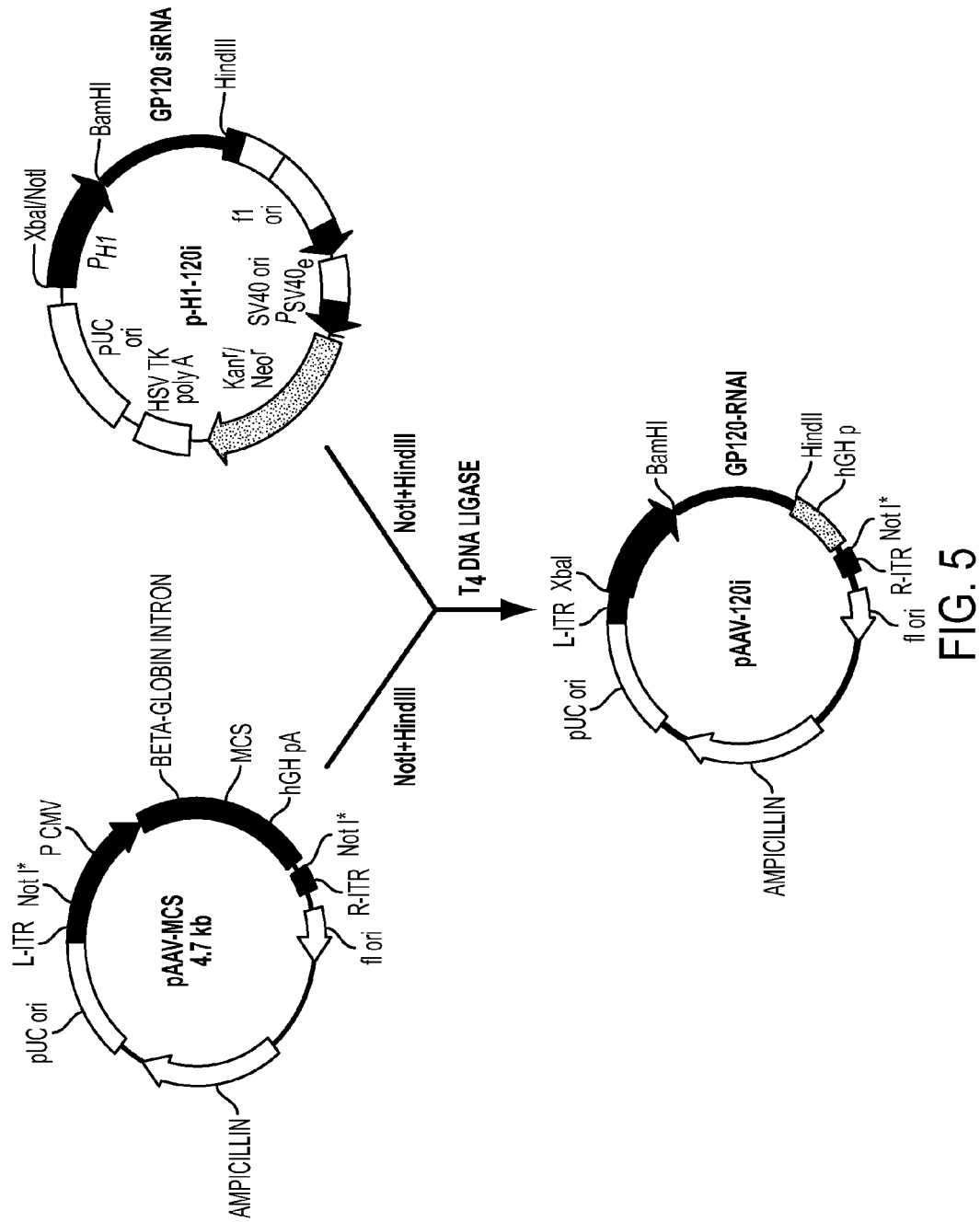

FIG. 5 Construction of plasmid pAAV-120i.

Figure 6:
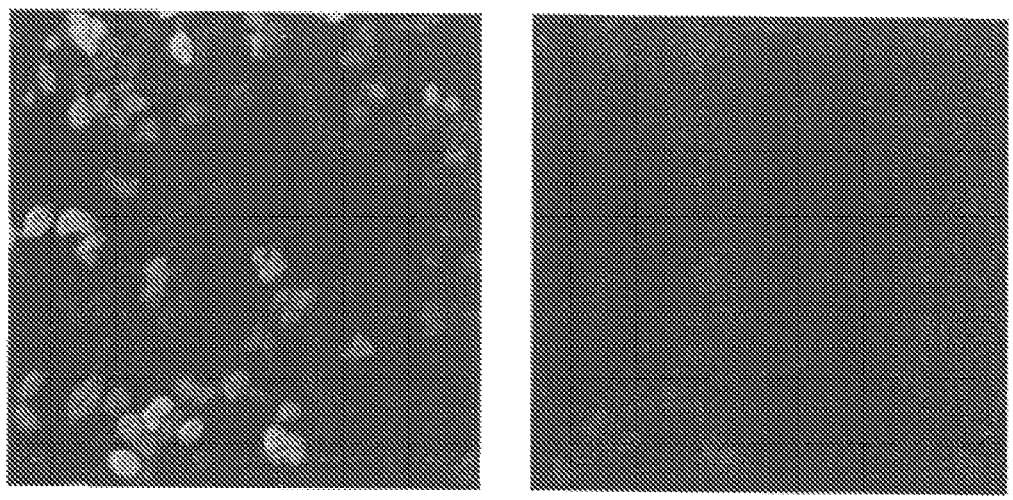

FIG. 6 GFP-GP120 expression was knocked down by hairpin-like double strand RNA expressed by recombinant AAV.

BEST APPROACHES TO REALIZE THE INVENTION

All the protocols are generally based on the protocols described in Molecular Cloning, 3$^{rd}$ edition.

EXAMPLE 1

Most Conserved HIV RNA Sequence

HIV genome sequences published were selected and separated into 70 nt fragments based on functional genes of HIV. Homology of every fragment with more than 140,000 sequences in Genebank (National Center of Biological Information, USA), EMBL (Nucleotide Sequence Database in Europe Molecular Biology Laboratory), DDBJ (Japan nucleotide database) and GDB (gene database) was analyzed by BlastN 2.2.4/2.2.5. The conserved RNA sequences were selected by the following criteria: (1) The sequence is equal or longer than 19 nt; (2) The sequence was 100% homology with at least 1000 HIV sequences in the database; (3) If 100% homology fragments can not be found, The sequences containing 1 mismatched nucleotide were included. The results of the analysis were shown in table 1 and table 2.

TABLE 1

Most conserved HIV RNA sequences found by homology analysis

| No | HIV gene | RNA sequence | |
|---|---|---|---|
| 1 | gag-pol | Aucaaugaggaagcugcagaaugg | (SEQ ID NO: 1) |
| 2 | gag-pol | Gggaagugacauagcaggaacuacuag | (SEQ ID NO: 2) |
| 3 | gag-pol | uaaauaaaauaguaagaauguauagcccu | (SEQ ID NO: 3) |
| 4 | env | Uauggguaccugugugga | (SEQ ID NO: 4) |
| 5 | env | Gccaauucccauacauuauugugc | (SEQ ID NO: 5) |
| 6 | Env | Uuaaauggcagucuagcagaa | (SEQ ID NO: 6) |
| 7 | Nef | Accacacacaaggcuacuucccugau | (SEQ ID NO: 7) |
| 8 | 3-UTR | Acagccgccuagcauuucaucac | (SEQ ID NO: 8) |
| 9 | LTR | Ggauggugcuucaagcuaguaccaguu | (SEQ ID NO: 9) |

TABLE 2

Homology analysis of the conserved RNA sequences with sequences in database

| No | HIV gene | Fragment size (nt) | HIV sequence compared | 100% homology sequences | Sequence (s) with 1nt mismatch |
|---|---|---|---|---|---|
| 1 | Gag-pol | 24 | 1050 | 1050 | 0 |
| 2 | Gag-pol | 27 | 1051 | 1050 | 1 |
| 3 | Gag-pol | 29 | 1050 | 1048 | 2 |
| 4 | env | 19 | 1050 | 1050 | 0 |
| 5 | env | 24 | 1050 | 1050 | 0 |
| 6 | env | 21 | 1050 | 1050 | 0 |
| 7 | nef | 26 | 1082 | 1082 | 0 |
| 8 | 3-UTR | 23 | 1070 | 1070 | 0 |
| 9 | LTR | 27 | 1069 | 1069 | 0 |

EXAMPLE 2

HIV env Gene Expression was Knocked Down by Chemically Synthesized Double Strand RNA Positive and negative (complement strand) RNA strand were synthesized according to the SEQ ID#1 with UU modification at 3' of the sequences.

```
5' uauggguaccuguguggauu    (SEQ ID NO: 10)

3' uuauaccccauggacacaccu   (SEQ ID NO: 11)
```

As showed in FIG. 1, plasmid pEGFPC1 (Clontech, Calif.) was double digested with EcoRI and BamHI at 37° C. for 1 hour. Large fragment was extracted and was used as vector; HIV gp120 gene was obtained by PCR using 2 ng HIV cDNA (Bru strain) as template plus gp120 primers (A:5' cggaat-tctaaagagcacaagacagtggac, (SEQ ID NO:12) B: 5' cggatec-tactctaccgtcagcgtcattga (SEQ ID NO:13) 100 ng each) in a buffer containing 2.5 u Pfu high fidelity DNA polymerase, dNTP 250 μmol/L, 2.5 mmol/L MgCl$_2$, 25 mmol/L TrisHCl (pH8.3). Polymerase chain reaction (PCR) was carried out using Perkin Elmer 9700 thermocycler (94° C. 30 s, 50° C. 30 s, 72° C. 90 s, 30 cycles), DNA fragment resulted PCR was double digested by EcoRI and BamHI (Biolabs) after being purified by Qiagen Gel Extraction Kit and ligated with the vector described above. The ligated mixture was transformed into *E. coli* JM109 (Promega), and the plasmid pEGFP-gp120 was obtained. Fusion protein of GFP and HIV gp120 should be expressed by transfection of the plasmid into mammalian cells.

HEK 293 cells (from ATCC) were co-transfected with 1 μg plasmid pEGFP-gp120 and 1 μg double strand RNA described above using LIPOFECTamine (rf. Manul from Invitrogen), The cells were assayed by fluorescent microscopy and the cell lysate were analyzed by immuno-blotting with anti-GFP antibody (Clontech) 36 h after transfection. A mock double strand RNA (rf. Ds RNA correspond HIV GAG gene, see EXAMPLE 3) was employed as control.

Results: As shown in FIG. 2, expression of the fusion protein was knocked down by env specific double strand RNA compared to the control. The experiment was repeated twice, and was shown as DsRNA1 and DsRNA2 respectively. As shown in FIG. 3, the expression level of GFP-HIV GP120 fusion protein was knocked down up to 80%.

EXAMPLE 3

HIV gag Gene Expression was Knocked Down by Synthesized Double Strand RNA

Based on the conserved gag RNA sequence (Seq ID#2 in table 1), a 21 nt oligonucleotides and its complement sequence was synthesized. The sequences contain 19 nt from Seq ID#2 and two U at 3' of each fragment. Double strand RNA was obtained by annealing.

```
5' gugacauagcaggaacuacuu    (SEQ ID NO: 14)

3' uucacuguaucguccuugaug    (SEQ ID NO: 15)
```

Gag gene from HIV (LAV-1, Bru isolate) was amplified and cloned into pEGFP C1 vector (Clontech, Calif.) as described in EXAMPLE 2, GFP-HIV gag fusion protein was expected to be expressed by the plasmid when it was transfected into cells.

The plasmid as well as double strand RNA was co-transfected into HEX 293 cells by LIPOFECTamine protocol, GFP-HIV gag protein was demonstrated to be knocked down by the double strand RNA compared to the mock double strand, as shown by the fluorescent microscopy of the cells 36 h after transfection.

EXAMPLE 4

Nef Gene Expression was Knocked Down by Synthesized Double Strand RNA

According to the conserved nef sequence (SEQ ID147 in table 1), a 21 nt oligo-nucleotide was synthesized with it complement RNA sequence, in which the 5' 19 nt was derived from SEQ ID#7 and two U was added to the 3' of each oligo-nucleotide. Double strand RNA was obtained by annealing.

```
5' accacacacaaggcuacuuuu    (SEQ ID NO: 16)

3' uuuggugugucguuccgaugaa   (SEQ ID NO: 17)
```

Gene encoding nef protein was amplified and cloned into pEGFPC1 as shown in example 2, and the GFP-Nef fusion protein was expected to be expressed by the cells containing the recombinant plasmid.

HEK 293 cells were co-transfected with the plasmid obtained and the double strand RNA synthesized, it has demonstrated that the expression of the GFP-HIV nef fusion protein was knocked down by the nef specific double strand RNA as compared to the mock double strand RNA, as shown by fluorescent microscopy 36 hours after transfection.

EXAMPLE 5

Expression of Other HIV Proteins could be Knocked Down by Synthesized Double Strand RNA (Tapbe 3)

TABLE 3

Expression of other HIV genes were knocked down by the novo double strand RNA

| No | | DsRNA | | Targeted HIV gene | Efficacy of inhibition |
|---|---|---|---|---|---|
| 1 | 5' | aucaaugaggaagcugcaguu | (SEQ ID NO: 18) | gag-pol | ++++ |
|   | 3' | uuuaguuacuccuucgacguc | (SEQ ID NO: 19) |   |   |
| 2 | 5' | guaagaauguauagcccuguu | (SEQ ID NO: 20) | gag-pol | +++ |
|   | 3' | uucauucuuacauaucgggac | (SEQ ID NO: 21) |   |   |
| 3 | 5' | uucccauacauuauugugcuu | (SEQ ID NO: 22) | env | +++ |
|   | 3' | uuaaggguauguaauaacacg | (SEQ ID NO: 23) |   |   |
| 4 | 5' | aaauggcagucuagcagaauu | (SEQ ID NO: 24) | env | +++ |
|   | 3' | uuuuuaccgucagaucgucuu | (SEQ ID NO: 25) |   |   |

注: +++ 60-80% inhibition, ++++ 80-100% inhibition.

EXAMPLE 6

Expression of HIV Envelope was Knocked Down by RNAi Expressed by Eukaryotic Vector Containing Double DNA Fragments Encoding Conserved Hairpin SiRNA DNA corresponding to the fragment of SeqID#5 RNA sequence shown at table 1 and its hybrid sequence (bold italic) were synthesized, double strand DNA fragment was obtained by annealing. BamHI and HindIII sites were included at its 5' and 3', respectively. There are 9 bp space between conserved sequence and its hybridization sequence. Fragment B is the complement sequence of fragment A:

A: 5' gatcccc*ttcccatacattattgtgc*ttcaagaga*gcacaataatgtatgggaa*ttttggaaa (SEQ ID NO: 26)

B: 5' agcttttccaaaaa*ttcccatacattattgtgct*ctcttgaa*gcacaataatgtatgggaa*ggg (SEQ ID NO: 27)

As shown in FIG. 4, Human H1 promoter was amplified by primer 1 (5'-TAATTAATGCGGCCGCAATTCGAACGCT-GACGTC-3') (SEQ ID NO:28) and primer 2 (5'-GCACTAG-TAAGCTTGGATCCGTGGICTCATACA-GAACTTATAAGATTCCC-3') (SEQ ID NO:29) using 1 µg human genomic DNA as templates and cloned into AseI and XbaI sites of plasmid pEGFP (Clontech). The ligated mixture was transformed into *E. coli* JM109, and the recombinant plasmid pH1 was obtained. Annealed double strand DNA fragment described was cloned into pH1 at its BamHI and HindIII sites, and a new recombinant plasmid, pH1-gp120i, was obtained. Hairpin RNA could be transcribed by RNA polymerase III in the cells harboring pH1-gp120i.

HEK293 cells were co-transfected with 4 µg pH1-gp120i plasmid (same amount of pH1 was used as control) and a plasmid expressing EGFP-HIV GP120. The differential expression of EGFP-HIV GP120 was assayed as described in Example 2. The results demonstrated that RNAi encoded by plasmid containing DNA fragment encoding hairpin RNA can effectively inhibit the expression of target HIV gene.

EXAMPLE 7

Expression of HIV GP120 was Knocked Down by RNAi Transcribed in the Cells Infected by Adenovirus Associated Virus (AAV) which Contain H1 Promoter and the Relevant DNA Fragment Encoding Hairpin RNA as Described in Example 6

As shown in FIG. 5, plasmid pAAV-MCS (Stratagene) was digested with NotI and HindIII; DNA fragment containing H1 promoter and DNA fragment encoding hairpin RNA corresponded to gp120 was obtained by digesting pH1-gp120 with NotI and HindIII. The fragment was ligated to vector by T4 DNA ligase, and plasmid pAAV-gp120i was constructed. HEK 293FT cells were co-transfected with the plasmid (4 µg), helping plasmid pHelper (1 µg, Stratagene) and plasmid pAAV-RC (2 µg Stratagene) by LIPOFECTamine, and empty vector (pAAV-MCS) was used as control. Recombinant AAV and control AAV was harvested 48 hour after transfection.

HEK 293 cells were transfected by pEGFP-GP120 (1 µg) as described and infected by the recombinant AAV encoding RNAi or empty AAV, fluorescent of GFP expressed was assayed 24 h after infection by fluorescent microscope.

As shown in FIG. 6, GFP-GP120 expression was significantly inhibited by the recombinant AAV which encoded hairpin RNA.

INDUSTRIAL APPLICABILITY

The invention was superior to the current technology as shown below:

Highly conserved RNA fragments in all published HIV genome were obtained by homology analysis. Double strand RNA derived from the highly conserved RNA could effectively knock down the expression of HIV gene. HIV gene expression could also inhibited by dsRNA encoded by plasmid as well as recombinant adenovirus associated virus containing corresponded DNA sequence.

---

What is claimed is:

1. An isolated nucleic acid molecule selected from the group consisting of:
   a single stranded RNA consisting of SEQ ID NO:7;
   a single stranded RNA consisting of SEQ ID NO:7 with two uracil nucleotides appended to the 5' terminus, the 3' terminus, or both;
   an siRNA comprising a double stranded RNA consisting of SEQ ID NO: 7 annealed to its complementary ribonucleotide sequence; and
   an siRNA comprising a double stranded RNA consisting of SEQ ID NO: 7 annealed to its complementary ribonucleotide sequence, with two uracil nucleotides appended to each 3' terminus, each 5' terminus, or both.

2. The nucleic acid molecule of claim 1, wherein said RNA is a single stranded RNA consisting of SEQ ID NO: 7 with two uracil nucleotides appended to the 5' terminus, the 3' terminus, or both, or a double stranded RNA consisting of SEQ ID NO: 7 annealed to its complementary ribonucleotide sequence, with two uracil nucleotides appended to each 3'-terminus, each 5'-terminus, or both.

3. An isolated hairpin RNA consisting of a stem part and a loop part,
   wherein said stem part is a double stranded RNA consisting of
   SEQ ID NO: 7 annealed to its complementary ribonucleotide sequence,
   or which stem part is a double stranded RNA consisting of SEQ ID NO: 7 annealed to its complementary ribonucleotide sequence with two uracil nucleotides appended to the 5'-terminus, the 3'-terminus, or both,
   and wherein said loop is a non-complementary spacer.

4. An isolated single-stranded or double-stranded DNA, wherein:
   1) said single-stranded DNA or one strand of said double-stranded DNA encodes the RNA or siRNA of claim 1, or its complementary sequence; or
   2) said single-stranded DNA or one strand of said double-stranded DNA encodes the RNA or siRNA of claim 2, or its complementary sequence; or
   3) said single-stranded DNA or one strand of said double-stranded DNA encodes the RNA of claim 3 or its complementary sequence.

5. An expression vector, wherein said vector comprising the DNA of claim 4.

6. A liposome encapsulating the RNA of any one of claims 1-3.

7. A liposome encapsulating the DNA of claim 4.

8. A liposome encapsulating the vector of claim 5.

* * * * *

SEQUENCE LISTING

<160> NUMBER OF SEQ ID NOS: 29

<210> SEQ ID NO 1
<211> LENGTH: 24
<212> TYPE: RNA
<213> ORGANISM: Lentivirus genera

<400> SEQUENCE: 1
aucaaugagg aagcugcaga augg        24

<210> SEQ ID NO 2
<211> LENGTH: 27
<212> TYPE: RNA
<213> ORGANISM: Lentivirus genera

```
<400> SEQUENCE: 2
gggaagugac auagcaggaa cuacuag                                    27

<210> SEQ ID NO 3
<211> LENGTH: 29
<212> TYPE: RNA
<213> ORGANISM: Lentivirus genera

<400> SEQUENCE: 3
uaaauaaaau aguaagaaug uauagcccu                                  29

<210> SEQ ID NO 4
<211> LENGTH: 19
<212> TYPE: RNA
<213> ORGANISM: Lentivirus genera

<400> SEQUENCE: 4
uaugggguac cugugugga                                             19

<210> SEQ ID NO 5
<211> LENGTH: 24
<212> TYPE: RNA
<213> ORGANISM: Lentivirus genera

<400> SEQUENCE: 5
gccaauuccc auacauuauu gugc                                       24

<210> SEQ ID NO 6
<211> LENGTH: 21
<212> TYPE: RNA
<213> ORGANISM: Lentivirus genera

<400> SEQUENCE: 6
uuaaauggca gucuagcaga a                                          21

<210> SEQ ID NO 7
<211> LENGTH: 26
<212> TYPE: RNA
<213> ORGANISM: Lentivirus genera

<400> SEQUENCE: 7
accacacaca aggcuacuuc ccugau                                     26

<210> SEQ ID NO 8
<211> LENGTH: 23
<212> TYPE: RNA
<213> ORGANISM: Lentivirus genera

<400> SEQUENCE: 8
acagccgccu agcauuucau cac                                        23

<210> SEQ ID NO 9
<211> LENGTH: 27
<212> TYPE: RNA
<213> ORGANISM: Lentivirus genera

<400> SEQUENCE: 9
ggauggugcu ucaagcuagu accaguu                                    27

<210> SEQ ID NO 10
<211> LENGTH: 21
<212> TYPE: RNA
<213> ORGANISM: Artificial Sequence
```

-continued

<220> FEATURE:
<223> OTHER INFORMATION: Chemically synthesized positive strand of
double-stranded RNA viral gene expression inhibitor

<400> SEQUENCE: 10
uaugggguac cuguguggau u 21

<210> SEQ ID NO 11
<211> LENGTH: 21
<212> TYPE: RNA
<213> ORGANISM: Artificial Sequence
<220> FEATURE:
<223> OTHER INFORMATION: Chemically synthesized negative strand of
double-stranded RNA viral gene expression inhibitor

<400> SEQUENCE: 11
uccacacagg uaccccauau u 21

<210> SEQ ID NO 12
<211> LENGTH: 30
<212> TYPE: DNA
<213> ORGANISM: Artificial Sequence
<220> FEATURE:
<223> OTHER INFORMATION: Chemically synthesized PCR primer

<400> SEQUENCE: 12
cggaattcta aagagcacaa gacagtggac 30

<210> SEQ ID NO 13
<211> LENGTH: 30
<212> TYPE: DNA
<213> ORGANISM: Artificial Sequence
<220> FEATURE:
<223> OTHER INFORMATION: Chemically synthesized PCR primer

<400> SEQUENCE: 13
cggatcctac tctaccgtca gcgtcattga 30

<210> SEQ ID NO 14
<211> LENGTH: 21
<212> TYPE: RNA
<213> ORGANISM: Artificial Sequence
<220> FEATURE:
<223> OTHER INFORMATION: Chemically synthesized positive strand of
double-stranded RNA viral gene expression inhibitor

<400> SEQUENCE: 14
gugacauagc aggaacuacu u 21

<210> SEQ ID NO 15
<211> LENGTH: 21
<212> TYPE: RNA
<213> ORGANISM: Artificial Sequence
<220> FEATURE:
<223> OTHER INFORMATION: Chemically synthesized negative strand of
double-stranded RNA viral gene expression inhibitor

<400> SEQUENCE: 15
guaguuccug cuaugucacu u 21

<210> SEQ ID NO 16
<211> LENGTH: 21
<212> TYPE: RNA
<213> ORGANISM: Artificial Sequence
<220> FEATURE:
<223> OTHER INFORMATION: Chemically synthesized positive strand of
double-stranded RNA viral gene expression inhibitor -continued

```
<400> SEQUENCE: 16
accacacaca aggcuacuuu u                                              21

<210> SEQ ID NO 17
<211> LENGTH: 21
<212> TYPE: RNA
<213> ORGANISM: Artificial Sequence
<220> FEATURE:
<223> OTHER INFORMATION: Chemically synthesized negative strand of
      double-stranded RNA viral gene expression inhibitor

<400> SEQUENCE: 17
aaguagccuu gugugugguu u                                              21

<210> SEQ ID NO 18
<211> LENGTH: 21
<212> TYPE: RNA
<213> ORGANISM: Artificial Sequence
<220> FEATURE:
<223> OTHER INFORMATION: Chemically synthesized positive strand of
      double-stranded RNA viral gene expression inhibitor

<400> SEQUENCE: 18
aucaaugagg aagcugcagu u                                              21

<210> SEQ ID NO 19
<211> LENGTH: 21
<212> TYPE: RNA
<213> ORGANISM: Artificial Sequence
<220> FEATURE:
<223> OTHER INFORMATION: Chemically synthesized negative strand of
      double-stranded RNA viral gene expression inhibitor

<400> SEQUENCE: 19
cugcagcuuc cucauugauu u                                              21

<210> SEQ ID NO 20
<211> LENGTH: 21
<212> TYPE: RNA
<213> ORGANISM: Artificial Sequence
<220> FEATURE:
<223> OTHER INFORMATION: Chemically synthesized positive strand of
      double-stranded RNA viral gene expression inhibitor

<400> SEQUENCE: 20
guaagaaugu cuagcccugu u                                              21

<210> SEQ ID NO 21
<211> LENGTH: 21
<212> TYPE: RNA
<213> ORGANISM: Artificial Sequence
<220> FEATURE:
<223> OTHER INFORMATION: Chemically synthesized negative strand of
      double-stranded RNA viral gene expression inhibitor

<400> SEQUENCE: 21
cagggcuaga cauucuuacu u                                              21

<210> SEQ ID NO 22
<211> LENGTH: 21
<212> TYPE: RNA
<213> ORGANISM: Artificial Sequence
<220> FEATURE:
<223> OTHER INFORMATION: Chemically synthesized positive strand of
      double-stranded RNA viral gene expression inhibitor
```

```
<400> SEQUENCE: 22
uucccauaca uuauugugcu u                                              21

<210> SEQ ID NO 23
<211> LENGTH: 21
<212> TYPE: RNA
<213> ORGANISM: Artificial Sequence
<220> FEATURE:
<223> OTHER INFORMATION: Chemically synthesized negative strand of
      double-stranded RNA viral gene expression inhibitor

<400> SEQUENCE: 23
gcacaauaau guaugggaau u                                              21

<210> SEQ ID NO 24
<211> LENGTH: 21
<212> TYPE: RNA
<213> ORGANISM: Artificial Sequence
<220> FEATURE:
<223> OTHER INFORMATION: Chemically synthesized positive strand of
      double-stranded RNA viral gene expression inhibitor

<400> SEQUENCE: 24
aaauggcagu cuagcagaau u                                              21

<210> SEQ ID NO 25
<211> LENGTH: 21
<212> TYPE: RNA
<213> ORGANISM: Artificial Sequence
<220> FEATURE:
<223> OTHER INFORMATION: Chemically synthesized negative strand of
      double-stranded RNA viral gene expression inhibitor

<400> SEQUENCE: 25
uucugcuaga cugccauuuu u                                              21

<210> SEQ ID NO 26
<211> LENGTH: 64
<212> TYPE: DNA
<213> ORGANISM: Artificial Sequence
<220> FEATURE:
<223> OTHER INFORMATION: Chemically-synthesized postiive strand of
      DNA fragment encoding hairpin SiRNA

<400> SEQUENCE: 26
gatccccttc ccatacatta ttgtgcttca agagagcaca ataatgtatg ggaattttttg   60 gaaa                                                                 64

<210> SEQ ID NO 27
<211> LENGTH: 64
<212> TYPE: DNA
<213> ORGANISM: Artificial Sequence
<220> FEATURE:
<223> OTHER INFORMATION: Chemically-synthesized negative strand of DNA
      fragment encoding hairpin SiRNA

<400> SEQUENCE: 27 agctttttcca aaaattccca tacattattg tgctctcttg aagcacaata atgtatggga   60
aggg                                                                 64

<210> SEQ ID NO 28
<211> LENGTH: 34
<212> TYPE: DNA
<213> ORGANISM: Artificial Sequence
<220> FEATURE:
<223> OTHER INFORMATION: Chemically-synthesized PCR primer
```

```
<400> SEQUENCE: 28
taattaatgc ggccgcaatt cgaacgctga cgtc                                  34

<210> SEQ ID NO 29
<211> LENGTH: 50
<212> TYPE: DNA
<213> ORGANISM: Artificial Sequence
<220> FEATURE:
<223> OTHER INFORMATION: Chemically-synthesized PCR primer

<400> SEQUENCE: 29
gcactagtaa gcttggatcc gtggtctcat acagaactta taagattccc                 50
```